US006987085B2

(12) United States Patent
Seki

(10) Patent No.: US 6,987,085 B2
(45) Date of Patent: Jan. 17, 2006

(54) SKIN CLEANSING COMPOSITIONS

(75) Inventor: Tsuyoshi Seki, Tokyo (JP)

(73) Assignee: Kao Corporation, Tokyo (JP)

( * ) Notice: Subject to any disclaimer, the term of this patent is extended or adjusted under 35 U.S.C. 154(b) by 17 days.

(21) Appl. No.: 10/864,493

(22) Filed: Jun. 10, 2004

(65) Prior Publication Data

US 2005/0020461 A1 Jan. 27, 2005

(30) Foreign Application Priority Data

Jun. 13, 2003 (JP) ............................. 2003-168903

(51) Int. Cl.
*A61K 7/50* (2006.01)

(52) U.S. Cl. ...................... 510/130; 510/141; 510/152; 510/153; 510/158; 510/159; 510/488; 510/481; 510/491; 424/70.1

(58) Field of Classification Search ................ 510/130, 510/136, 119, 121, 129, 152
See application file for complete search history.

(56) References Cited

U.S. PATENT DOCUMENTS

| | | | |
|---|---|---|---|
| 5,360,581 | A | 11/1994 | Rizvi et al. |
| 5,858,343 | A | 1/1999 | Szymczak |
| 5,998,354 | A | 12/1999 | Turowski-Wanke et al. |
| 2002/0035047 | A1 | 3/2002 | Sebillotte-Arnaud et al. |
| 2003/0078172 | A1 | 4/2003 | Guiramand et al. |
| 2003/0224955 | A1 | 12/2003 | Ribery et al. |

FOREIGN PATENT DOCUMENTS

| | | |
|---|---|---|
| DE | 101 40 150 A1 | 2/2003 |
| EP | 1 225 214 A2 | 7/2002 |
| JP | 59-75999 | 4/1984 |
| JP | 1-149715 | 6/1989 |
| JP | 5-255049 | 10/1993 |
| JP | 6-506964 | 8/1994 |
| JP | 10-226798 | 8/1998 |
| JP | 2002-68961 | 3/2002 |
| WO | WO 92/19712 | 11/1992 |

*Primary Examiner*—Necholus Ogden
(74) *Attorney, Agent, or Firm*—Oblon, Spivak, McClelland, Maier & Neustadt, P.C.

(57) ABSTRACT

The present invention relates to a skin cleansing composition containing from 20 to 50% by weight of fatty acids and salts thereof, wherein the content of fatty acids having 20 to 24 carbon atoms is from 10 to 30% by weight of the total fatty acid components, and a weight ratio of fatty acids having not more than 15 carbon atoms to fatty acids having not less than 16 carbon atoms is in a range of from 20:80 to 50:50. The skin cleansing composition has many benefits such as high foamability, creamy foam quality, superior cleansing performance and rinsing property, low irritativeness and good storage stability, and gives a moist skin feeling after cleansing.

6 Claims, No Drawings

SKIN CLEANSING COMPOSITIONS

FIELD OF THE INVENTION

The present invention relates to a skin cleansing composition having benefits such as high foamability and creamy foam quality.

BACKGROUND OF THE INVENTION

Conventionally, inexpensive skin cleansing agents of fatty acid soaps having high cleansing performance and good foamability have been used as skin cleansing agents such as a facial wash. As raw materials of these skin cleansing agents, fatty acids (whose main components are saturated or unsaturated fatty acids having 8 to 18 carbon atoms) obtained by hydrolyzing natural fats and oils derived from plants and animals, such as beef tallow, coconut oil, palm oil and palm kernel oil, are mainly used.

Among fatty acid soaps prevalently used in skin cleansing agents containing fatty acid soaps as a main cleansing base, those of lauric acid (12 carbon atoms) or myristic acid (14 carbon atoms), which has a relatively short chain length, have defects such as giving a tight skin feeling after cleansing although they have a high water-solubility due to a low Krafft point. On the other hand, those of palmitic acid (16 carbon atoms) or stearic acid (18 carbon atoms), which has a longer chain length, have defects such as a low water-solubility and somewhat low foamability due to a high Krafft point although they give a mild feeling to skin.

No satisfactory cleansing compositions have been found so far in spite of the effort to develop cleansing compositions with improved foamability, safety, application feeling and the like, considering characteristics of these fatty acids. And thus a further improved cleansing composition has been desired.

Fatty acids having not less than 20 carbon atoms have seldom been used as a cleansing base due to their low water-solubility, insufficient foamability and unsatisfactory foam quality. However, there have been some proposals as described below. There have been some studies, for example, on transparent solid soaps incorporated with 0.5 to 6.0% by weight of a linear saturated fatty acid having 20 to 26 carbon atoms based on the total amount of fatty acids to enhance transparency of the solid soap (JP-A-59-75999); a pearl-like gloss dispersion having good storage stability, which contains 5 to 30% by weight of behenic acid and/or behenate salts (JP-A-10-226798, U.S. Pat. No. 5,998,354); a skin cleansing composition incorporated with 0.05 to 5% by weight of a saturated fatty acid having not less than 20 carbon atoms based on the total amount of the composition, to stabilize tone of the skin cleansing composition containing clay minerals (JP-A-1-149715); a skin cleansing agent incorporated with a specific higher fatty acid soap and a condensed ricinoleic acid polyglycerin ester, to improve stability thereof at high and low temperatures (JP-A-2002-68961); a hair conditioning shampoo composition containing 0.5 to 20% by weight of a fatty acid having a long chain of 18 to 36 carbon atoms (JP-A-5-255049, U.S. Pat. No. 5,360,581); and a solid cast composition containing 3 to 15% by weight of behenic acid soap (WO92/19712).

SUMMARY OF THE INVENTION

The present invention provides a skin cleansing composition containing from 20 to 50% of fatty acids and salts thereof, by weight of the skin cleansing composition, wherein the content of fatty acids having 20 to 24 carbon atoms is from 10 to 30% by weight of the total fatty acid components, and wherein a weight ratio of fatty acids having not more than 15 carbon atoms to fatty acids having not less than 16 carbon atoms is in a range of from 20:80 to 50:50.

DETAILED DESCRIPTION OF THE INVENTION

The present invention relates to a skin cleansing composition having benefits such as high foamability, creamy foam quality, superior cleansing performance and rinsing property, low skin irritativeness and good storage stability, and gives moist skin feeling after cleansing.

The present inventor has found that the above purpose can be attained by incorporating, in a fatty acid composition containing fatty acids and salts thereof, fatty acids having 20 to 24 carbon atoms in a specific amount and setting the ratio of fatty acids having not more than 15 carbon atoms to fatty acids having not less than 16 carbon atoms within a specific range.

The skin cleansing composition of the present invention contains fatty acids and salts thereof, and contains a fatty acid having 8 to 24 carbon atoms as a constituent of the fatty acids.

A counter ion constituting the fatty acid salt includes alkaline metals such as sodium and potassium, basic amino acids, organic amines and the like. Among these, an alkaline metal salt is preferable and a potassium salt is more preferable.

The neutralization degree of the fatty acids is preferably 60 to 100%, more preferably 65 to 95% and still more preferably 70 to 90%, in view of foamability and aging stability.

One or more fatty acids and the salts thereof may be used in combination and are contained in an amount of from 20 to 50% by weight, preferably from 20 to 45% by weight and more preferably from 20 to 40% by weight based on the total composition. An amount below 20% by weight may result in low foamability and poor foam quality, while an amount above 50% by weight may cause a tight skin feeling after cleansing.

The fatty acids and salts thereof constituting the composition of the present invention contain from 10 to 30% by weight, preferably from 12 to 28% by weight and more preferably from 15 to 25% by weight of a fatty acids having 20 to 24 carbon atoms, based on the total amount of the fatty acids and salts thereof. A content below 10% by weight in the composition causes a tight skin feeling, fails to give moist skin feeling after cleansing and lowers storage stability. On the other hand, a content above 30% by weight results in low foamability and poor foam quality.

The fatty acid having 20 to 24 carbon atoms is preferably a linear saturated fatty acid having 20 to 24 carbon atoms, including arachic acid (20 carbon atoms), behenic acid (22 carbon atoms) and lignoceric acid (24 carbon atoms), and is used in combination of one or more kinds. Among these, arachic acid and behenic acid are preferable.

Few fatty acids having 20 to 24 carbon atoms are contained in fats and oils derived from plants and animals, such as beef tallow, palm oil, palm kernel oil and castor oil, which are usually used as fatty acids for fatty acid soap-based cleansing compositions. Coconut oil and olive oil contain arachic acid in an amount as small as and not higher than 1% by weight, while rapeseed oil and peanut oil contain about from 1 to 3% by weight of arachic acid and behenic acid.

Few of these long-chain fatty acids have been used as raw materials of skin cleansing compositions although they have been sometimes used as a stability-improving agent of an emulsified composition such as cream (JP-A-56-18908) or as a pearl-like gloss furnishing agent (JP-A-10-226798, U.S. Pat. No. 5,998,354). As mentioned above, nothing has been known about the effect of lipophilic, long-chain fatty acids having 20 to 24 carbon atoms when they are included in a large amount in a fatty acid soap as a main cleansing base.

In the present invention, the weight ratio of the fatty acids having not more than 15 carbon atoms to the fatty acids having not less than 16 carbon atoms, both of which constitute the fatty acids and the salts thereof, is in a range of from 20:80 to 50:50, preferably 25:75 to 45:55 and more preferably 30:70 to 40:60. If the ratio of the fatty acids having not more than 15 carbon atoms is below 20:80, a composition with sufficient foamability cannot be obtained, while if the ratio is above 50:50, a composition with a tight skin feeling after cleansing and low aging stability will be obtained.

The fatty acids having not more than 15 carbon atoms are preferably lauric acid or myristic acid.

The fatty acids having not less than 16 carbon atoms include the above-described fatty acids having 20 to 24 carbon atoms and the fatty acids constituting the salts thereof, as well as palmitic acid, stearic acid, isostearic acid, oleic acid and the like, among which palmitic acid and stearic acid are preferable.

The skin cleansing composition of the present invention can further contain glycols or glycol ethers. Specifically, ethylene glycol, propylene glycol, 1,3-butylene glycol, diethylene glycol, dipropylene glycol, isoprene glycol, polyethylene glycol (average molecular weight of not higher than 2,000), polypropylene glycol (average molecular weight of not higher than 1,500), diethylene glycol monoethyl ether and the like are included, among which dipropylene glycol and diethylene glycol monoethyl ether are preferable.

One or more kinds of these glycols or glycol ethers can be used and are contained preferably in an amount of from 3 to 30% by weight and more preferably from 5 to 25% by weight based on the total composition, from the view points of foamability, stability, and solubility of fatty acids having 20 to 24 carbon atoms and the salts thereof during manufacturing.

In addition, the skin cleansing composition of the present invention can contain polyalcohols having at least 3 hydroxyl groups in the molecule. Specifically, glycerin, sorbitol, mannitol, erythritol, xylitol, maltitol, trehalose, sucrose, polyglycerin and the like are included, among which glycerin, sorbitol, erythritol and xylitol are preferable.

One or more kinds of these polyalcohols can be used and also can be used together with the above-described glycols or glycol ethers. These polyalcohols are contained preferably in an amount of from 3 to 30% by weight and more preferably from 5 to 28% by weight based on the total composition from the view points of reducing a tight skin feeling and giving a moist skin feeling after cleansing.

The skin cleansing composition of the present invention preferably contains water in an amount of from 20 to 70% by weight, more preferably from 25 to 60% by weight and still more preferably from 30 to 50% by weight.

In addition to the above-described components, the skin cleansing composition of the present invention can contain further components, for example, surfactants other than fatty acid salts, moisturizing agents, oily components, disinfectants, anti-inflammatories, antiseptics, chelating agents, thickeners, salts, pearling agents, scrubbing agents, perfumes, cool skin feeling agents, pigments, UV-ray absorbers, antioxidants, plant extracts and the like.

The skin cleansing composition of the present invention can be manufactured by mixing each component and can take any form of liquid, cream, paste or solid. Cream and paste are preferable in view of applicability. The composition can be applied to a facial wash, a makeup remover, a body shampoo, a hand soap or the like.

EXAMPLES

The following examples further describe and demonstrate embodiments of the present invention. The examples are given solely for the purpose of illustration and are not to be construed as limitations of the present invention.

Examples 1–7 and Comparative Examples 1–5

Skin cleansing compositions shown in Table 1 were manufactured and evaluated for foamability, foam quality, rinsing property, irritativeness, moist skin feeling after cleansing, cleansing performance and aging stability. The results are summarized in Table 1. The neutralization degree of the fatty acids in any of the examples shown in Table 1 is 80% based on the total fatty acids.

(Evaluation Method)

(1) Foamability, Foam Quality, Rinsing Property, Irritativeness and Moist Skin Feeling After Cleansing:

Ten expert panelists performed facial cleansing tests using each composition to organoleptically evaluate foamability (easiness of foaming and volume of foam), foam quality (creamy feeling and elasticity), rinsing property (quickness to rinse off and absence of slimy feeling), irritativeness (tight skin feeling, dry skin feeling) and moist skin feeling after cleansing, in accordance with the following organoleptic evaluation criteria.

(Organoleptic Evaluation Criteria)

◎: not less than 8 of 10 expert panelists judged good

○: 6 to 7 of 10 expert panelists judged good

Δ: 4 to 5 of 10 expert panelists judged good

X: not more than 3 of 10 expert panelists judged good (2) Cleansing Performance:

A lipstick of 5 mg having a composition similar to sebum was applied to a 3 cm×5 cm area of the inner side of forearm skin and left as it is for 30 minutes. The applied area was then massaged for 30 seconds using 1 g of each composition shown in Table 1 in an attempt to remove stains. After the area was rinsed with water, each composition was judged in accordance with the following cleansing performance-evaluation criteria. The above lipstick composition consists of 60% by weight of ester oil, 20% by weight of wax, 10% by weight of cholesterol ester and 10% by weight of pigment.

(Cleansing Performance-evaluation Criteria)

◎: all stains are removed

○: most of the stains are removed

Δ: a few stains are not removed

X: only a few stains are removed (3) Storage Stability

Each composition was filled into a transparent plastic container of 120 ml volume with a cap and left standing at 5° C. and 40° C. for one month and then subjected to visual observation. Each composition was judged in accordance with the following storage stability-evaluation criteria.

(Storage Stability-evaluation Criteria)

⊚: No change is observed

○: A minor change is observed but there is no practical problem

Δ: A few smears or flocculates are observed

X: Srated substances or flocculates are observed

Table 1

TABLE 1-1

| Components | Examples | | | | | | |
|---|---|---|---|---|---|---|---|
| (% by weight) | 1 | 2 | 3 | 4 | 5 | 6 | 7 |
| Lauric Acid | 2.5 | 2.6 | 2.3 | 0 | 3 | 2.5 | 2.5 |
| Myristic Acid | 8 | 8.4 | 7.4 | 13.5 | 4.6 | 8 | 8 |
| Palmitic Acid | 6 | 6.3 | 5.6 | 4.5 | 9 | 6 | 6 |
| Stearic Acid | 7.5 | 7.9 | 6.9 | 5.5 | 7 | 7.5 | 7.5 |
| Behenic Acid | 6 | 5 | 8 | 6 | 6 | 6 | 6 |
| Potassium Hydroxide | 5.2 | 5.2 | 5.1 | 5.1 | 5 | 5.2 | 5.2 |
| Dipropylene glycol | 15 | 15 | 15 | 15 | 15 | 15 | 0 |
| Glycerin | 10 | 10 | 10 | 10 | 10 | 0 | 10 |
| Purified Water | balance | balance | balance | balance | balance | balance | balance |
| Ratio of $C_{20-24}$ Fatty Acids to total Fatty Acids (% by weight) | 20 | 16.5 | 26.5 | 20 | 20 | 20 | 20 |
| Ratio by weight of Fatty Acids of 15 or less carbon atoms to Fatty Acids of 16 or more carbon atoms | 35:65 | 36:64 | 32:68 | 46:54 | 26:74 | 35:65 | 35:65 |
| Fatty Acids and Salts thereof (% by weight) | 33.6 | 33.8 | 33.8 | 33.1 | 33.1 | 33.6 | 33.6 |
| Neutralization Degree (%) | 80 | 80 | 80 | 80 | 80 | 80 | 80 |
| Foamability | ⊚ | ⊚ | ○ | ⊚ | ○ | ⊚ | ○ |
| Foam quality | ⊚ | ⊚ | ⊚ | ○ | ⊚ | ⊚ | ○ |
| Rinsing property | ⊚ | ⊚ | ⊚ | ○ | ⊚ | ⊚ | ⊚ |
| Irritativeness | ⊚ | ○ | ⊚ | ○ | ⊚ | ○ | ⊚ |
| Moist feeling | ⊚ | ⊚ | ⊚ | ⊚ | ⊚ | ○ | ⊚ |
| Cleansing performance | ○ | ○ | ⊚ | ○ | ○ | ○ | ○ |
| Storage stability (5° C.) | ⊚ | ⊚ | ⊚ | ⊚ | ⊚ | ○ | ○ |
| Storage stability (40° C.) | ⊚ | ○ | ○ | ○ | ⊚ | ○ | ○ |

TABLE 1-2

| Components | Comparative Examples | | | | |
|---|---|---|---|---|---|
| (% by weight) | 1 | 2 | 3 | 4 | 5 |
| Lauric Acid | 3.5 | 2.5 | 2.5 | 4 | 1.2 |
| Myristic Acid | 10.2 | 8 | 8 | 16 | 4 |
| Palmitic Acid | 7.6 | 8 | 2 | 2 | 9 |
| Stearic Acid | 8.5 | 10 | 2.5 | 2.5 | 11 |
| Behenic Acid | 0 | 1.5 | 15 | 6 | 6 |
| Potassium Hydroxide | 5.5 | 5.3 | 4.9 | 5.6 | 5.2 |
| Dipropylene glycol | 10 | 10 | 10 | 10 | 10 |
| Glycerin | 10 | 10 | 10 | 10 | 10 |
| Purified Water | balance | balance | balance | balance | balance |
| Ratio of $C_{20-24}$ Fatty Acids to total Fatty Acids (% by weight) | 0 | 5 | 50 | 17.5 | 19 |
| Ratio by weight of Fatty Acids of 15 or less carbon atoms to Acids of 16 or more carbon atoms | 46:54 | 35:65 | 35:65 | 66:34 | 17:83 |
| Fatty Acids and Salts thereof (% by weight) | 33.6 | 33.7 | 33.4 | 34.4 | 34.8 |
| Neutralization degree (%) | 80 | 80 | 80 | 80 | 80 |
| Foamability | ⊚ | ⊚ | X | ⊚ | X |
| Foam property | ○ | ○ | X | ⊚ | Δ |
| Rinsing property | ○ | ○ | Δ | ○ | ○ |
| Irritativeness | X | X | ○ | X | ○ |
| Moist feeling | X | Δ | ⊚ | Δ | ○ |
| Cleansing performance | Δ | Δ | ○ | ○ | ⊚ |
| Storage stability (5° C.) | ○ | ○ | X | ○ | Δ |
| Storage stability (40° C.) | X | X | Δ | X | ○ |

Example 8 (Facial Wash)

A facial wash having the following composition was manufactured by mixing each component.

The content of fatty acids and salts thereof is 33.6% by weight, and the content of fatty acids having 20 to 24 carbon atoms in the total fatty acids is 20% by weight. The weight ratio of fatty acids having not more than 15 carbon atoms to fatty acids having not less than 16 carbon atoms is 35:65, and neutralization degree of the fatty acids is 80% based on the total fatty acids.

(Components)

| | |
|---|---|
| lauric acid | 2.5 (% by weight) |
| myristic acid | 8.0 |
| palmitic acid | 6.0 |
| stearic acid | 7.5 |
| arachic acid | 1.0 |
| behenic acid | 5.0 |
| potassium hydroxide | 5.2 |
| dipropylene glycol | 5.0 |
| diethylene glycol monoethyl ether | 5.0 |
| glycerin | 10.0 |
| sorbitol | 10.0 |
| sodium cocoylmethyl taurate | 1.5 |
| polyethylene glycol of high polymerization degree | 0.02 |
| dibutylhydroxytoluene | 0.1 |
| EDTA·2Na | 0.2 |
| hydroxyethanediphosphonic acid | 0.3 |
| purified water | balance |

Example 9 (Facial Wash)

A facial wash having the following composition was manufactured by mixing each component.

The content of fatty acids and salts thereof is 43.4% by weight, and the content of fatty acids having 20 to 24 carbon atoms in the total fatty acids is 17% by weight. The weight ratio of fatty acids having not more than 15 carbon atoms to fatty acids having not less than 16 carbon atoms is 45:55, and the neutralization degree of the fatty acids is 75% based on the total fatty acids.

(Components)

| | |
|---|---|
| lauric acid | 2.9 (% by weight) |
| myristic acid | 14.6 |
| palmitic acid | 6.6 |
| stearic acid | 8.2 |
| arachic acid | 1.0 |
| behenic acid | 5.6 |
| potassium hydroxide | 6.4 |
| dipropylene glycol | 9.0 |
| diethylene glycol monoethyl ether | 5.0 |
| glycerin | 10.0 |
| lauramide propylbetaine liquid (30%) | 5.0 |
| glycerol monostearate ester | 2.0 |
| glycyrrhizinic acid dipotassium salt | 0.1 |
| chelating agent | proper amount |
| plant extract | proper amount |
| perfume | proper amount |
| purified water | balance |

Example 10 (Body Shampoo)

A body shampoo having the following composition was manufactured by mixing each component.

The content of fatty acids and salts thereof is 27.5% by weight, and the content of fatty acids having 20 to 24 carbon atoms in the total fatty acids is 17% by weight. The weight ratio of fatty acids having not more than 15 carbon atoms to fatty acids having not less than 16 carbon atoms is 50:50, and neutralization degree of the fatty acids is 90% based on the total fatty acids.

(Components)

| | |
|---|---|
| lauric acid | 8.0 (% by weight) |
| myristic acid | 4.0 |
| palmitic acid | 8.0 |
| arachic acid | 0.6 |
| behenic acid | 3.4 |
| potassium hydroxide | 5.0 |
| dipropylene glycol | 8.0 |
| glycerin | 10.0 |
| laurylhydroxysulfobetaine liquid (30%) | 10.0 |
| coconut fatty acid diethanolamide | 1.0 |
| ethylene glycol distearate | 3.0 |
| antioxidant | proper amount |
| antiseptic | proper amount |
| metal blocking agent | proper amount |
| pH adjuster | proper amount |
| perfume | proper amount |
| purified water | balance |

Any skin cleansing composition obtained in Examples 8 to 10 is superior in foamability, foam quality, rinsing property, low irritativeness, moist skin feeling after cleansing, cleansing performance and aging stability.

The skin cleansing composition of the present invention has benefits such as high foamability, creamy foam quality, superior cleansing performance and rinsing property, low irritativeness and good aging stability, and gives moist skin feeling after cleansing.

What is claimed is:

1. A skin cleansing composition comprising:

20 to 50% of fatty acids having 8 to 24 carbon atoms and salts thereof, by weight of the skin cleansing composition, wherein a fatty acid moiety having 20 to 24 carbon atoms is from 10 to 30% by weight in said fatty acids and salts thereof, and wherein a weight ratio of a fatty acid moiety having 8 to 14 carbon atoms to a fatty acid moiety having 16 to 24 carbon atoms is in a range of from 20:80 to 50:50 in said fatty acids and salts thereof.

2. The skin cleansing composition according to claim 1, wherein the fatty acid moiety having 20 to 24 carbon atoms is selected from the group consisting of arachic acid, behenic acid, and mixtures thereof.

3. The skin cleansing composition according to claim 1, further comprising glycols or glycol ethers.

4. The skin cleansing composition according to claim 1, further comprising polyalcohols having not less than 3 hydroxyl groups in the molecule.

5. The skin cleansing composition according to claim 1, comprising 20 to 70% of water, by weight of the skin cleansing composition.

6. The skin cleansing composition according to claim 1, wherein a neutralization degree of the fatty acids is 60 to 100%.

* * * * *